US00PP20121P3

(12) United States Plant Patent
Ruter

(10) Patent No.: US PP20,121 P3
(45) Date of Patent: Jun. 23, 2009

(54) ***HIBISCUS* PLANT NAMED 'PANAMA RED'**

(50) Latin Name: *Hibiscus radiatus*
Varietal Denomination: Panama Red

(75) Inventor: John Ruter, Tifton, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 11/881,889

(22) Filed: Jul. 30, 2007

(65) Prior Publication Data

US 2009/0038040 P1 Feb. 5, 2009

(51) Int. Cl.
*A01H 5/00* (2006.01)

(52) U.S. Cl. ..... Plt./257
(58) Field of Classification Search ..... Plt./257
See application file for complete search history.

(56) References Cited

U.S. PATENT DOCUMENTS

| | | | |
|---|---|---|---|
| PP11,772 | P2 | 2/2001 | Bergman |
| PP11,854 | P2 | 5/2001 | Fleming et al. |
| PP11,857 | P2 | 5/2001 | Fleming et al. |
| PP13,631 | P2 | 3/2003 | Fleming et al. |
| PP13,745 | P2 | 4/2003 | Zwetzig et al. |
| PP13,746 | P2 | 4/2003 | Zwetzig et al. |
| PP13,752 | P2 | 4/2003 | Zwetzig et al. |
| PP13,913 | P3 | 6/2003 | Fleming et al. |
| PP15,091 | P2 | 8/2004 | Whitcomb |
| PP16,155 | P3 | 12/2005 | Leue |
| PP16,286 | P2 | 2/2006 | Mostul |
| PP16,669 | P3 | 6/2006 | Fleming et al. |

*Primary Examiner*—June Hwu
(74) *Attorney, Agent, or Firm*—Davis Wright Tremaine LLP

(57) ABSTRACT

*Hibiscus* 'Panama Red' is an ornamental variety, crossed and cultivated in Georgia. The plants of the new Hibiscus display an intense red color in high light, deeply cut foliage, stable foliage color, very large flowers, thrives in hot an humid conditions, and flowers heavily during short days (November to April) in zone 10. 'Panama Red' can be grown in the garden or in a container.

3 Drawing Sheets

Latin Name:*Hibiscus* 'Panama Red' is of the genus and species *Hibiscus radiatus*.

Variety denomination: The new *Hibiscus* claimed is of the variety denominated 'Panama Red.'

CROSS-REFERENCE TO RELATED APPLICATIONS

This patent application is related to co-pending U.S. patent application Ser. No. 11/881,930, invented by the same Inventor, assigned to the same Assignee, and filed simultaneously with, the present application. The present application *Hibiscus* 'Panama Red' is the maternal parent plant of cross-referenced *Hibiscus* 'Panama Bronze.'

BACKGROUND OF THE INVENTION

The present invention relates to a new and distinct cultivar of *Hibiscus*, botanically known as *Hibiscus acetosella,* and herein referred to as 'Panama Red.'

The new *Hibiscus* is a product of a planned breeding program conducted by the Inventor in Tifton, Ga. The objective of the *Hibiscus* breeding program is to create new plant cultivars with ornamental leaf distinctions and thrive in hot and humid conditions.

The new *Hibiscus* originated from a discovery of a seedling made by the Inventor in 2004, of an unnamed and unpatented red selection of the *Hibiscus acetosella,* wherein both the male and female parent are *Hibiscus acetosella,* wherein both the male and female parent are *Hibiscus acetosella.*

Asexual reproduction of the new *Hibiscus* by vegetative terminal cuttings in a controlled environment in Tifton, Ga.

since 2004, has shown that the unique features of this new *Hibiscus* are stable and reproduced true to type in successive generations.

BRIEF SUMMARY OF THE INVENTION

The cultivar 'Panama Red' has not been observed under all possible environmental conditions. The phenotype may vary somewhat with variations in environment and cultural practices such as temperature and light intensity without, however, any variance in genotype.

The following traits have been repeatedly observed and are determine to be the unique characteristics of 'Panama Red:'

1. Rounded growth habit;
2. Dissect leaves;
3. Stable foliage color;
4. Rich dark red foliage in low light;
5. Blackish-purple foliage in high light;
6. Flowers heavily under short days (November through April) in zone 10; and
7. Thrives in hot and humid conditions.

Plants of the new *Hibiscus* can be compared to its parents, *Hibiscus acetosella,* an example of which is known as *Hibiscus* 'Red Shield.' Plants of the new *Hibiscus* differ from 'Red Shield' in the following characteristics:

1. Plants of the new *Hibiscus* a nearly blackish-purple in high light and a rich, dark red in low light compared to a less intense red in 'Red Shield.'

2. Plants of the new *Hibiscus* have a more rounded growth habit compared to 'Red Shield.'
3. Plants of the new *Hibiscus* have more dissect leaves compared to 'Red Shield'.
4. Plants of the new *Hibiscus* have more petiole prickles compared to 'Red Shield.'

Plants of the new *Hibiscus* can be compared to its progeny, 'Panama Bronze' (co-pending patent application). Plants of the new *Hibiscus* differ from 'Panama Bronze' in the following characteristics:

1. Plants of the new *Hibiscus* display a nearly blackish-purple in high light and a rich, dark red in low light compared to 'Panama Bronze,' which shows an intense bronze color in high light and a green color in low light.
2. Plants of the new *Hibiscus* have flowers that are one third smaller compared to 'Panama Bronze.'
3. Plants of the new *Hibiscus* have less dissect leaves than 'Panama Bronze.'
4. Plants of the new *Hibiscus* are more dense compared to 'Panama Bronze.'

DETAILED BOTANICAL DESCRIPTION

Figure 1:
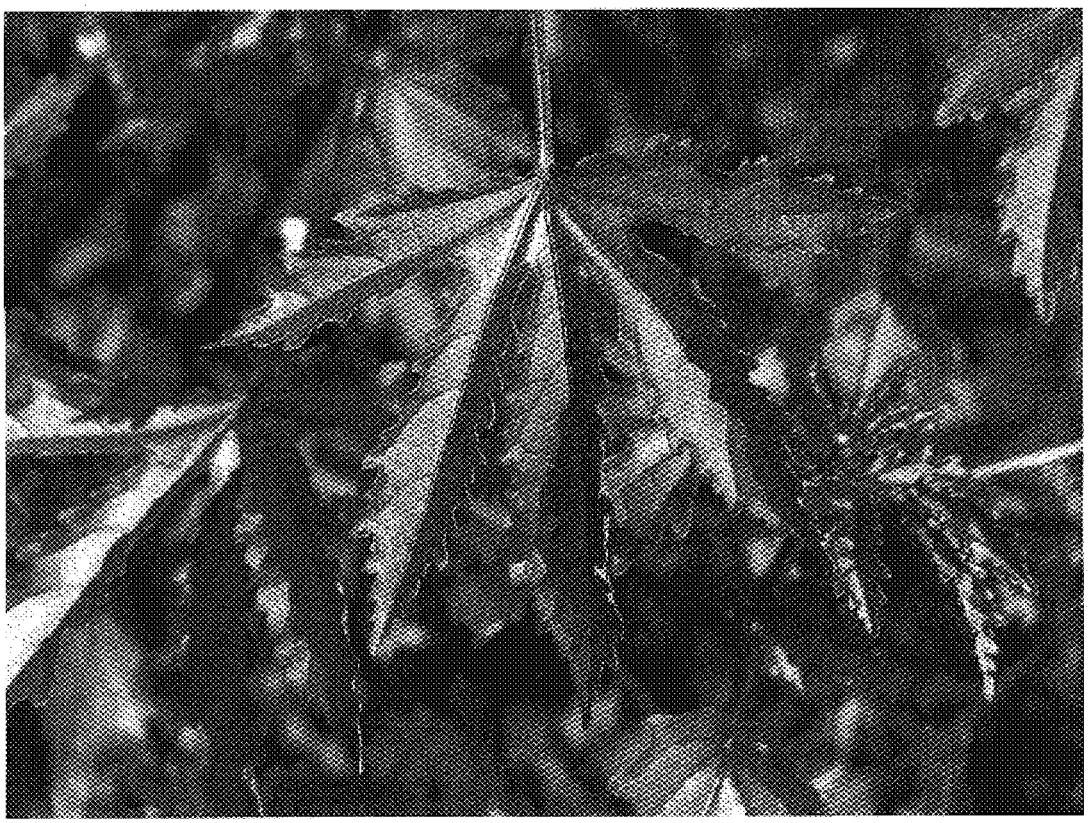
FIG. 1 is a photograph of 'Panama Red' showing the rounded growth habit.
Figure 2:
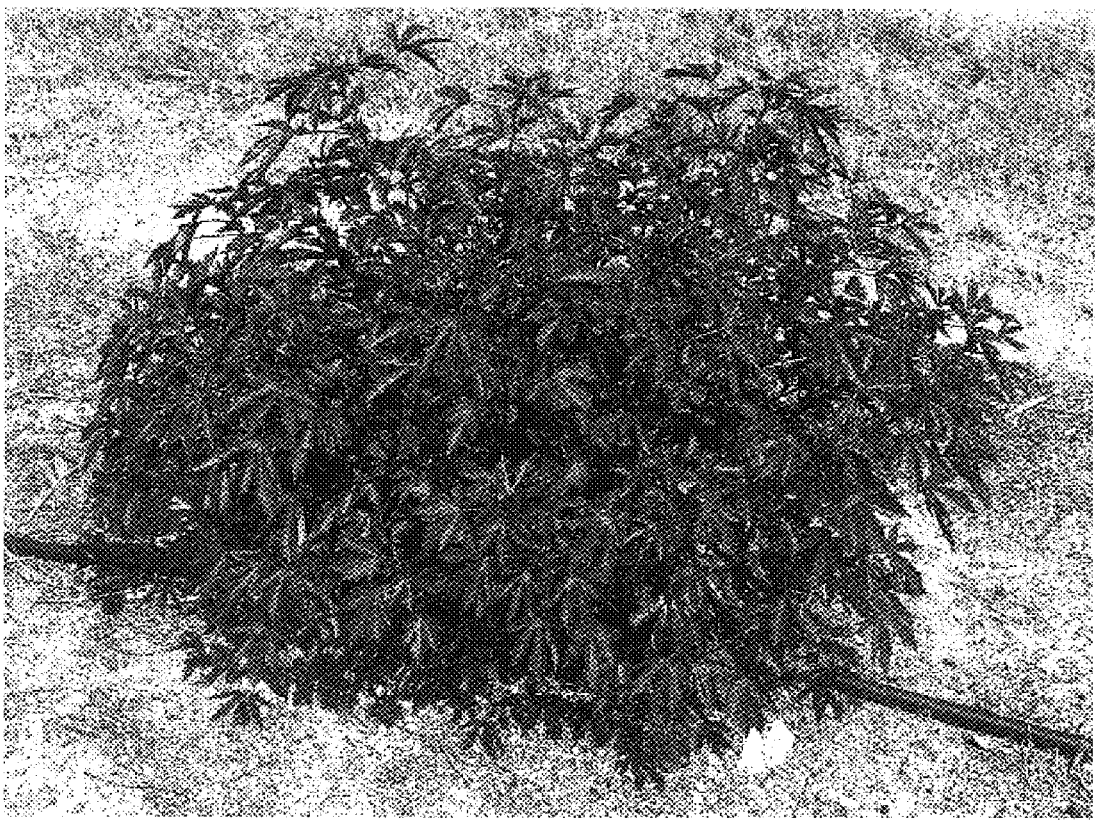
FIG. 2 is a photograph of a leaf of 'Panama Red' showing foliage color and dissect characteristics.
Figure 3:
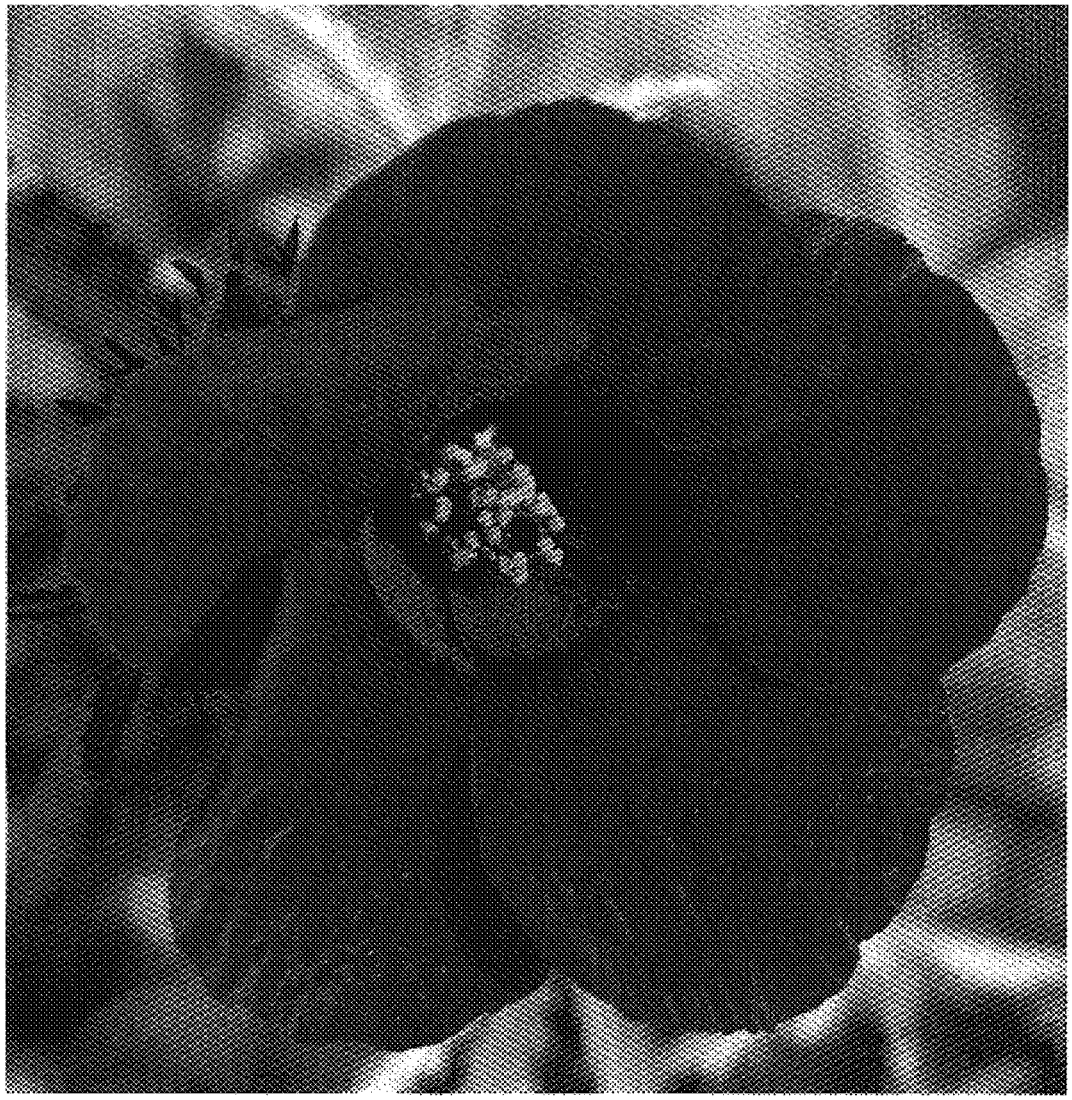
FIG. 3 is a photograph of a flower of 'Panama Red'.

The following observations, measurements and values describe plants grown in Athens, Ga. by Allan Armitage and Stephanie Anderson. During the growing of the plants, day temperatures ranges from 50° F. to 104° F. and night temperatures ranges from 35° F. to 80° F. In the description, color references are made to the Royal Horticultural Society (R.H.S.). Colour Chart, 1995, and 2001 Editions except where general terms of ordinary dictionary meaning are used.

I. Habit: Round to upright.

II. Size of plant:
- *A. Height.*—5–6' (0.6–0.9 m).
- *B. Width.*—2–3' (0.6–0.9 m).

III. Stem:
- *A. Color* (*RHS*).—60A.
- *B. Length.*—3–4' (0.9–1.2 m).
- *C. Diameter.*—3–5 mm.
- *D. Pubescence.*—None.
- *E. Shape.*—Round.
- *F. Odor* (*of bruised stem*).—None.
- *G. Internode length.*—4–5 cm.

IV. Leaf:
- *A. color* (*RHS*) *low light.*— 1. upper 139A. 2. lower 148B.
- *Color* (*RHS*) *high light.*— 1. upper N77A. 2. lower 187C.
- *C. Mature size* (*L×W*).—9.5×12 cm.
- *D. Apex.*—Acuminate.
- *D. Base.*—Truncate.
- *E. Margin.*—Crenate.
- *F. Shape.*—Palmate.
- *G. Lobes* (*present absent*).—1. number.—3–5.
- *H. Pubescence.*—None.
- *I. Arrangement on stem.*—Alternate.
- *J. Venation.*—Pinnipalmate.
- *K. Texture.*—Glabrous.

V. Petiole:
- *A. Length.*—6–7 cm.
- *B. Shape.*—Round.
- *C. Color* (*RHS*).—187A.
- *D. Pubescence.*—None.
- *E. Diameter.*—0.3 cm.

VI. Flower:
- *A. Inflorescence.*—None, solitary. 1. Number of individual flowers per stem 5–10. 2. Average size of fully opened flower 10–12 cm. 3. Lastingness of bloom 1 day. 4. Flower season November through April.
- *B. Individual flower.*—1. Axillary, terminal axillary. 2. Symmetry radial. 3. Petals 5. a. size (L×W) 5.25×4 cm. b. shape spatutate. c. apex rounded. d. base truncate. e. margin entire. f. color at peak of bloom 1) apex 187C. 2) base 187A. 4. pedicels a. color (RHS) 187C. b. pubescence none. c. length 1–2 mm. 5. Sepals a. number 5. b. size (L×W) 1.8×0.7 cm. c. shape linear. d. pubescence none. e. color lower surface (RHS) 144B. 6. Stamens a. number 23–25. b. size (L×W) 0.4×4.8 cm. c. color (RHS) 184B. d. pollen color (RHS) 163A. e. pubescence none. 7. Pistils a. number 1. b. size of style (L×W) 2.5×0.3 cm. C. color of style (RHS) 185B. d. color of stigma (RHS) 187A. 8. Bracts a. number 9–11. b. size (L×W) 1.8×0.5 cm. c. color, lower(RHS) 126A. d. shape spatulate.

C. Fruit: No fruit seen.

D. Seed: No seed seen.

What is claimed is:

1. A new and distinct variety of *Hibiscus* plant named 'Panama Red', substantially as illustrated and described herein.

* * * * *